United States Patent
Lechot et al.

(10) Patent No.: US 8,679,124 B2
(45) Date of Patent: Mar. 25, 2014

(54) DISPOSABLE ACETABULAR REAMER FROM FLAT STOCK

(75) Inventors: André Lechot, Orvin (CH); Sarah Claude, La Chenalotte (FR); Philippe Fehlbaum, Lignieres (CH); Patrick White, West Chester, PA (US); Didier Guelat, Porrentruy (CH)

(73) Assignee: Greatbatch Medical S.A., Orvin (CH)

(*) Notice: Subject to any disclaimer, the term of this patent is extended or adjusted under 35 U.S.C. 154(b) by 1570 days.

(21) Appl. No.: 11/960,754

(22) Filed: Dec. 20, 2007

(65) Prior Publication Data
US 2009/0163921 A1 Jun. 25, 2009

(51) Int. Cl.
*A61B 17/32* (2006.01)
*A61B 17/16* (2006.01)
*A61B 17/88* (2006.01)
*A61F 2/46* (2006.01)

(52) U.S. Cl.
USPC .............................................. 606/80; 606/81

(58) Field of Classification Search
USPC ........................... 606/91, 79–81, 84, 85, 180
See application file for complete search history.

(56) References Cited

U.S. PATENT DOCUMENTS

| | | | |
|---|---|---|---|
| 4,023,572 A * | 5/1977 | Weigand et al. | 606/81 |
| 6,475,221 B1 * | 11/2002 | White et al. | 606/80 |
| 2003/0220647 A1 * | 11/2003 | McCallum et al. | 606/81 |
| 2006/0095041 A1 * | 5/2006 | Fehlbaum et al. | 606/81 |
| 2006/0129157 A1 * | 6/2006 | Desarzens et al. | 606/81 |
| 2006/0189994 A1 * | 8/2006 | Wolford et al. | 606/80 |
| 2006/0195110 A1 * | 8/2006 | White et al. | 606/81 |

* cited by examiner

*Primary Examiner* — Michael T Schaper
(74) *Attorney, Agent, or Firm* — Michael F. Scalise (57) ABSTRACT

A disposable reamer is provided, made up of a base and a thin-walled, perforated cutting body of flat metal stock affixed thereto. The base and body may be molded together or assembled together in a mechanical manner. The body is optionally formed so as to comprise a plurality of appendages connected at a center so as to improve die forming of the body into a final desired shape while at the same time minimizing stress-induced deformation in the body.

29 Claims, 7 Drawing Sheets

DISPOSABLE ACETABULAR REAMER FROM FLAT STOCK

CROSS REFERENCE TO RELATED APPLICATIONS

This application claims priority to U.S. provisional application Ser. No. 60/871,780 of the same name, filed Dec. 23, 2006, the content of which is incorporated herein by reference.

BACKGROUND OF THE INVENTION

This invention relates to tools for cutting bone, in particular, to reamers for cutting the cotyloid cavity of the acetabulum in the event of the replacement of the hip joint by a prosthetic cup.

Tools for cutting bone are often difficult to clean, and prions, soft tissue embedded in the tool from some prior use, are often difficult to remove. It is considered the most certain manner in which to ensure that no cross contamination occurs between uses is to provide a cutting tool that is intended for a single use. After such use, the cutting tool is simply discarded.

Acetabular reamers in the prior art are generally press-formed out of stamped, flat metal stock. However, in the typical such case, the hemispherical form that results after press-forming can include deformities, considering the severe working and stresses induced in the materials as the flat stock is formed up into a hemispherical shape. To obtain an accurate result with minimum warpage, such reamers must be made with complex and expensive machinery. Consequently, the costs for such prior art reamers are high. High costs of manufacture mean high final cost. Customers which pay a significant amount for a tool are not likely to discard such tools after a single use.

Nothing herein is to be construed as an admission that the present invention is not entitled to antedate such cited material by virtue of prior invention.

What is needed therefore is a tool for cutting bone that is simple to manufacture at low cost and therefore disposable.

Still further, what is needed therefore is a method of manufacturing a disposable reamer that provides an accurate hemispherical form and thus ensures accurate cutting.

SUMMARY OF THE INVENTION

An at least partially disposable reamer is provided, made up of a circular base to which a press-formed, thin-walled, perforated cutting body of flat metal stock may be mechanically affixed. Once affixed, the assembly is rigid enough for cutting bone, yet may be disassembled so as to permit partial disposal. Prior to press-forming, the flat metal body is stamped out of flat metal stock, optionally having a plurality of appendages connected at a center. The base and body may be molded together or assembled together in a mechanical manner.

An object of the invention is that the appendages assure improved die forming of the body into a final desired shape while at the same time minimizing stress-induced deformation in the body.

DETAILED DESCRIPTION OF THE PREFERRED EMBODIMENT(S)

Figure 1A:
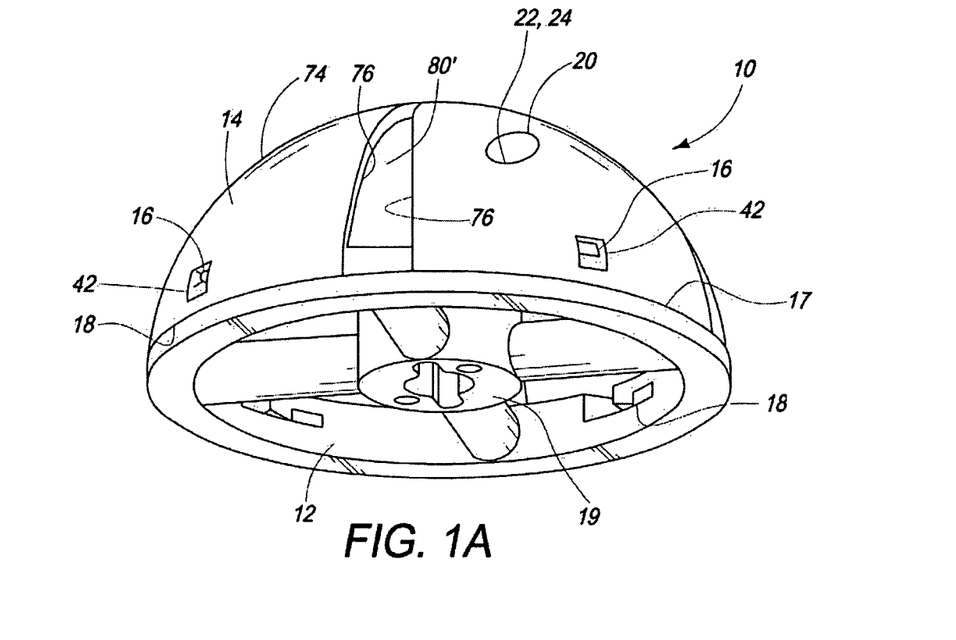
FIG. 1A is a perspective view of the disposable reamer of the invention.

Referring now to FIG. 1A, a reamer assembly 10 is made up of a base 12 and a cutting body 14 having locking interfaces 16 which lock with the base so as to permit interlocking therebetween. Locking interface 18 may be used for mechanical locking of the base 12 and cutting body 14 together.

Figure 1B:
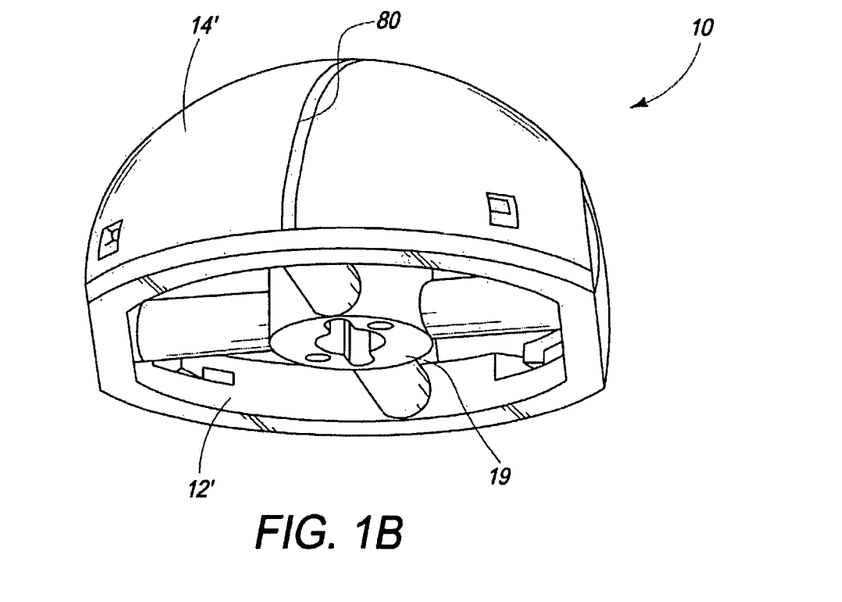
FIG. 1B is a perspective view of an alternate embodiment of the disposable reamer of the invention.
Figure 2:
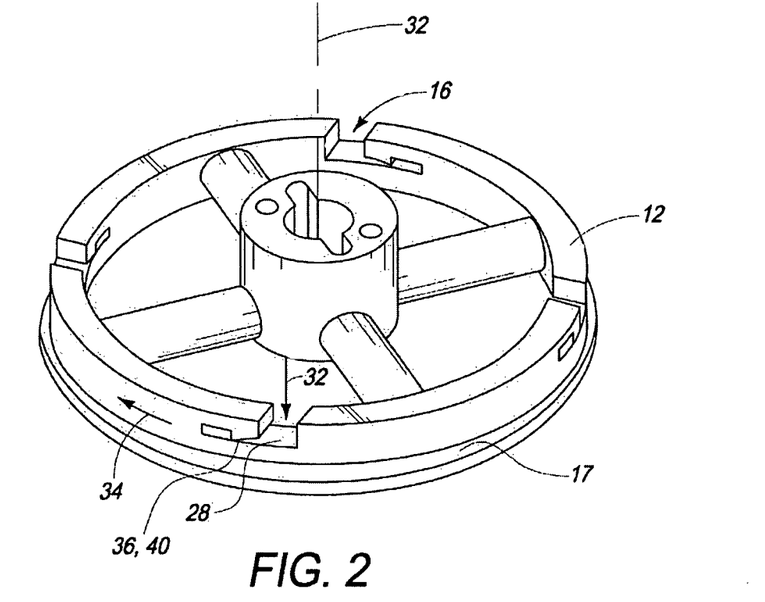
FIG. 2 is a perspective view showing the base of the reamer assembly of the invention.

Referring to FIG. 2, the base 12 is rigid, preferably made of a biocompatible plastic, and has a form which is circular, preferably including a stabilizing flange 17, against which the equatorial edge 18 of the cutting body 14 may abut. The base 12 includes an interface 19 FIGS. 1A and 1B) for interfacing with a holder (not shown), such as that described in U.S. Provisional Application No. 60/971406, filed 21 Dec., 2006, the content of which is incorporated herein by reference, connected to a rotating power source (not shown).

The cutting body 14 is a die-formed or press-formed, thin walled, convex member having perforations 20 thereon formed at cutting sites 22. Cutting teeth 24 are formed adjacent the perforations 20, which are distributed on the cutting body 14 so as to evenly cut bone when rotated with a cutting tool (not shown) in the acetabulum, in order to prepare the same for reception of a prosthesis (not shown)

Referring now to FIG. 1B, an alternate embodiment is shown, in which a reamer assembly 10' has a base 12' which is not circular, but rather formed to minimize it's insertion profile during minimally invasive surgery, such as described in U.S. patent application Ser. No. 10/510,934 filed Aug. 1, 2002, the content of which is incorporated by reference hereto. In this embodiment, a cutting body 14' has a corresponding form.

Referring now to FIG. 2, the base 12, 12' and the cutting body 14, 14' interlock via, for example, a snap-type, bayonet interface 16 comprised of a bayonet slot 28 which runs in a direction parallel to the axis 32 of rotation of the reamer assembly 10, when rotated for cutting, then doglegs in, a circumferential direction 34, at which point is found a locking device 36 such as a spur 40 which ensures that the connection 42 therebetween is of a rigidity sufficient to permit cutting while also, where desired, separation of the base 12 from the cutting body 14.

Figure 3A:
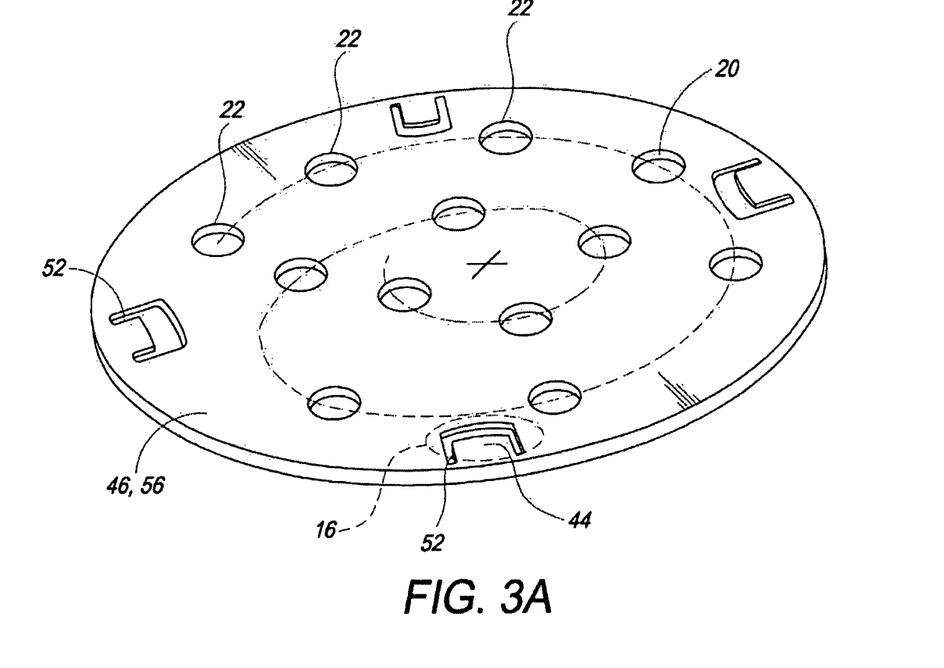
FIG. 3A is a perspective view of a blank from which the cutting body of the reamer assembly of the invention is made.
Figure 3B:
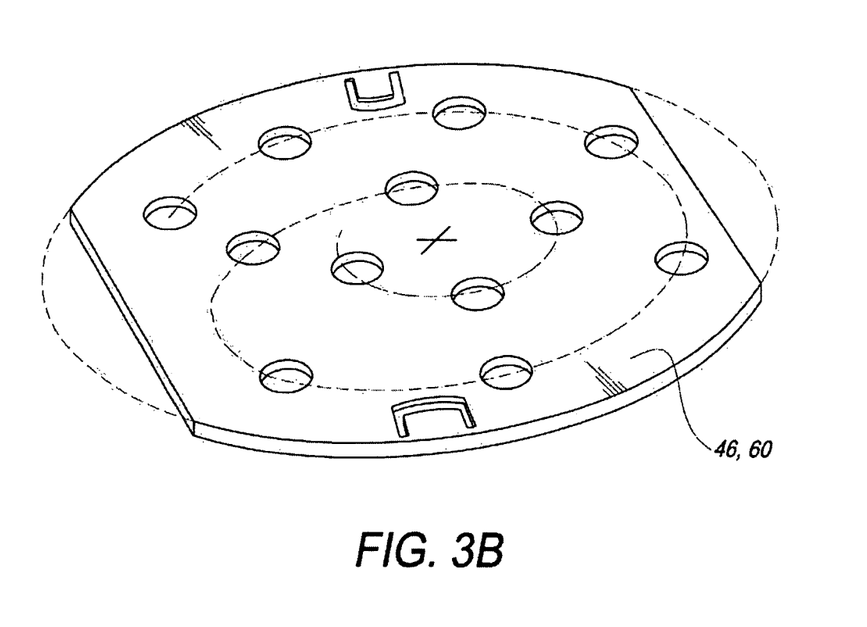
FIG. 3B is a perspective view of an alternate blank from which the cutting body of the reamer assembly of the invention is made.

Referring now to FIG. 3A, in one embodiment, the locking interface 16 of the cutting body 14 is a simple tab 44 which, after perforation, is die-formed at 90 degrees to the plane of the blank 46 from which the cutting body 14 is formed. The circumferential direction 34 is chosen so that the base 12 and cutting body 14 tend to lock together when the reamer assembly 10 cuts bone.

It is contemplated to provide reamer assemblies 10, 10' in several embodiments, among them, an embodiment of a fully disposable reamer assembly and a partially disposable reamer assembly. In embodiments where it is contemplated only to dispose of the cutting body 14 and not the base 12, the bayonet slot 28 is formed so as to permit removal of the base 12 from the cutting body 14. This can be accomplished by, for example, forming the spur 40 and or leading edge 52 of the tab 44 so as to permit removal after application of a certain torque, or by providing a tool (not shown) which slides between the spur 40 and tab 44, so as to disable the spur such that it no longer retains the cutting body 14.

Figure 3C:
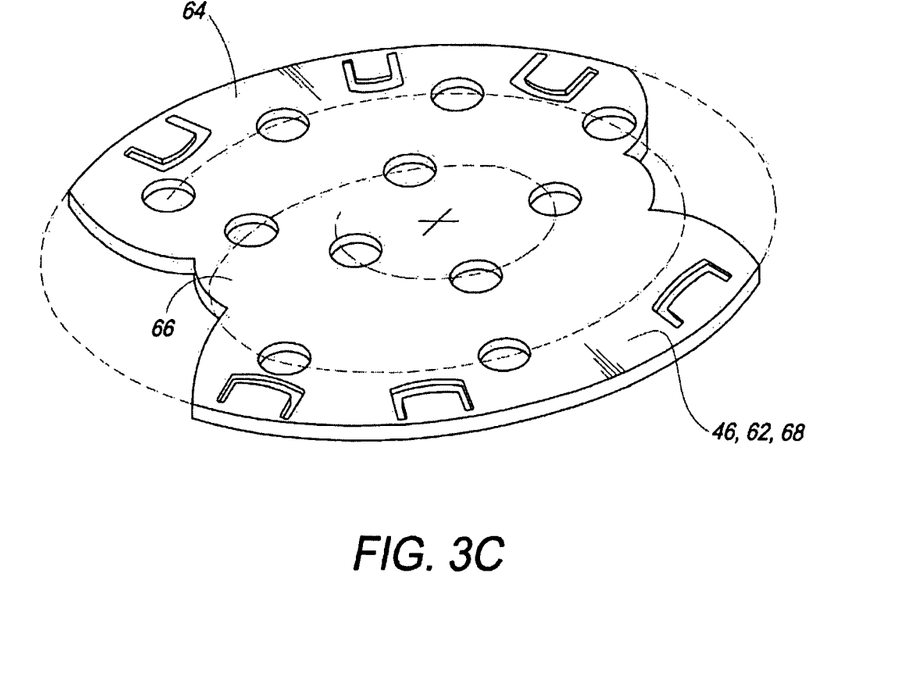
FIG. 3C is a perspective view of an alternate blank from which the cutting body of the reamer assembly of the invention is made.
Figure 3D:
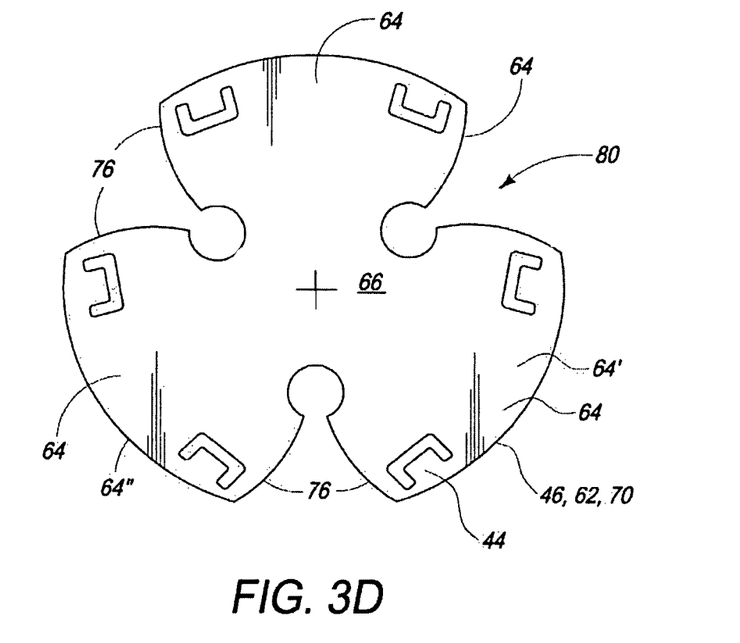
FIG. 3D is a perspective view of an alternate blank from which the cutting body of the reamer assembly of the invention is made.

Referring now to FIGS. 3A to 3E, in an important aspect of the invention, the blank 46 from which the cutting body 14 is formed is progressively die formed. The blank 46 may be a disk 56 or a partial disk 60, in a manner known for forming a conventional acetabular reamer, or a complex disk 62 having forms having two or more appendages 64 connected at a center 66. Referring in particular to FIG. 3C, the blank 46 having two appendages 64 connected at a center 66 is a bow tie blank 68. Referring in particular to FIG. 3D, the blank 46 having three appendages 64 connected at a center 66 resembles a three-leaf clover and is referred to herein as a three-appendage blank 70. The blank 46 having four appendages connected at a center 66 is a Maltese cross blank 72. The inventors have learned that blanks 46 with appendages 64 may be efficiently die-formed with less overall deformation and thus, such a design is suitable for heavy forming of less ductile materials such as 420 stainless steel, which are usually associated with cutting materials. Thus the die costs less and/or has a longer useful life, thereby reducing the cost of each reamer assembly 10, 10'.

Referring again to FIG. 3B, the partial disk 60, when fully formed, attaches to a partially circular base 12' so as to minimize the insertion profile of the reamer during minimally invasive surgery ("MIS"). The bow tie blank 68 may be used in this MIS application as well.

Figure 3E:
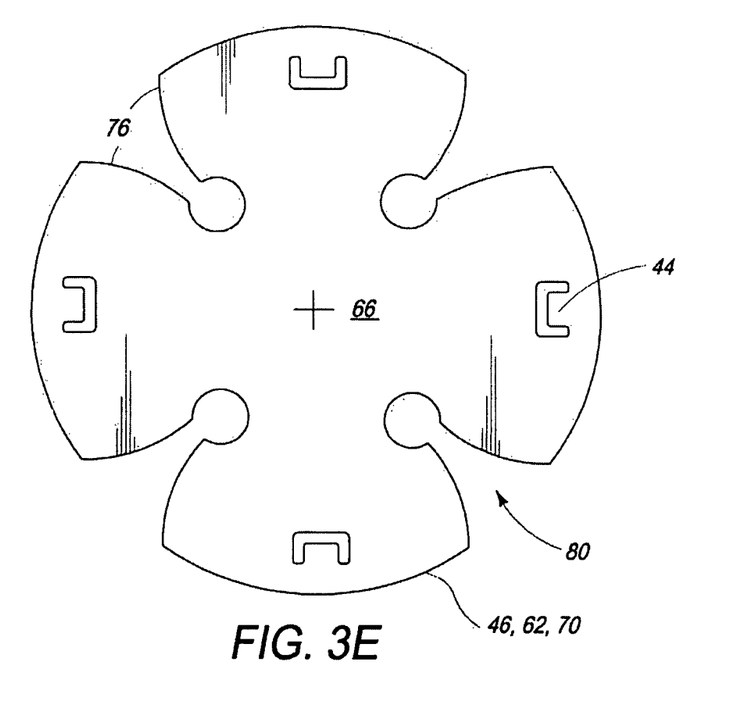
FIG. 3E is a perspective view of an alternate blank from which the cutting body of the reamer assembly of the invention is made.

Referring now to FIGS. 3D and 3E, the three-appendage blank 70 and the Maltese cross blank 72 are suitable for die-forming into a standard hemispherical form 74 as the form can be selected so as to, after die forming, completely occupy the hemispherical shape, wherein adjacent edges 76 butt up one against the other so as to close the gap 80 between such adjacent appendages 64' and 64''. Alternatively, a considerable gap 80' (FIG. 1A) may be left.

Figure 4A:
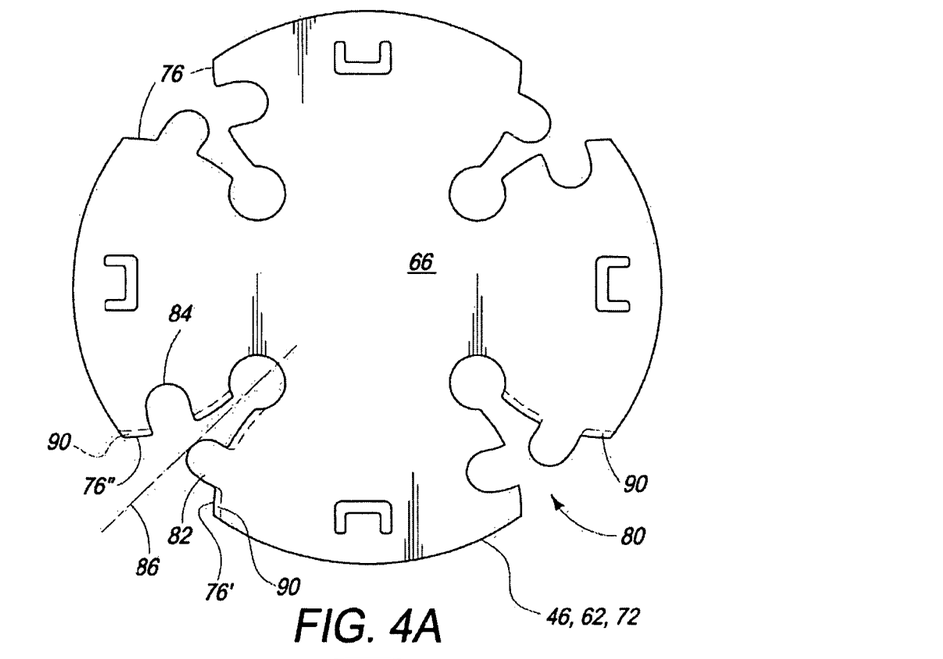
FIG. 4A is a perspective view of a further alternate blank from which the cutting body of the reamer assembly of the invention is made.
Figure 4B:
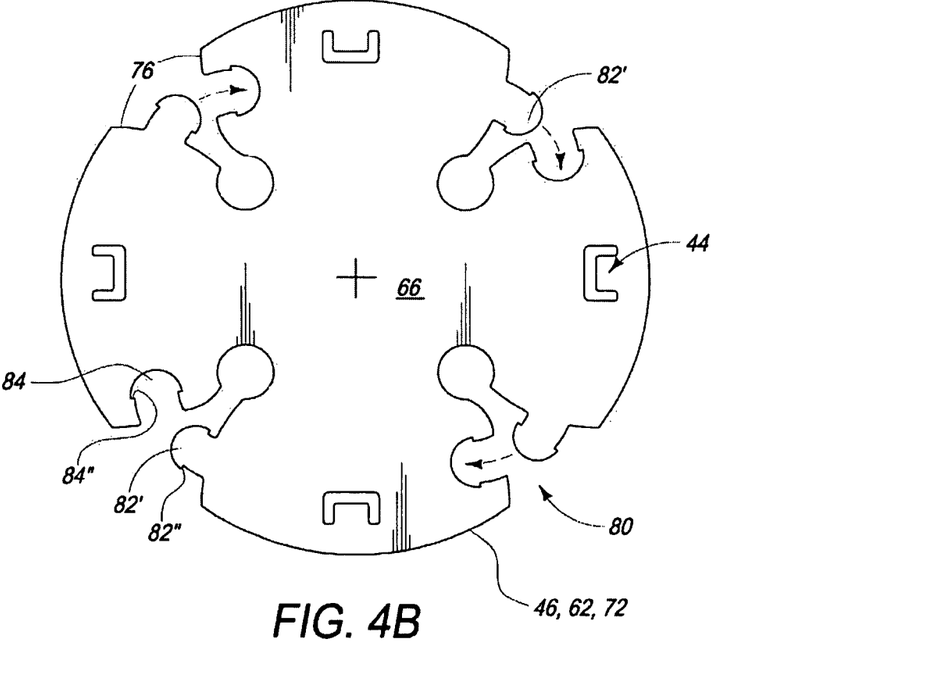
FIG. 4B is a perspective view of a further alternate blank from which the cutting body of the reamer assembly of the invention is made.

Referring now to FIGS. 4A and 4B, optionally, adjacent edges 76' and 76'' include male and female interlocks 82 and 84, respectively, which interlock upon completion of the die-forming operation, to help rigidize the cutting form 14. In the embodiment shown, the interlocks help rigidize the cutting form 14 along a line of longitude 86. Alternatively, the interlocks 82' and 84' include spurs 82'' which interlock with catches 84'' in order to rigidize the cutting form 14 latitudinally as well.

In order to minimize chatter when the reamer assembly 10 is in operation cutting bone, it may be necessary to specially form one or the other of the adjacent edges 76', 76'' (leading or trailing) so that it is radiused, or has a slightly curved lip 90 which is curved upwardly or downwardly, with the choice made based on experimental results. At present, the trailing edge (i.e., the edge of an appendage 64 which does not directly faces bone as it is being cut) being curved up slightly (perhaps over a latitudinal length of about 50 thousandths of an inch) tends to ensure that bone does not catch on the adjacent leading edge. However, having the adjacent leading edge (i.e., the edge of the appendage 64 that directly faces bone as it is being cut) curved down slightly helps avoid chatter as well.

Figure 5:
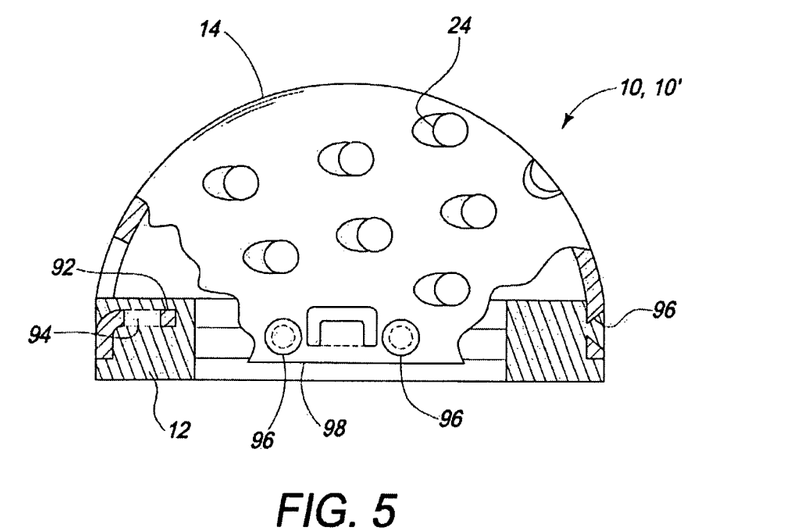
FIG. 5 is a side, partial break-away view of the reamer assembly of the invention.

Referring now to FIG. 5, in an alternate embodiment, a reamer assembly 10, 10' may be made in which the interlock between the base 12 and cutting body 14 is accomplished via an insert-molding in which, for example, a large tab 92 having a hole 94 therein, is formed inwardly, about which the base 12 is molded. In addition, or alternatively, holes 96 adjacent the equatorial edge 98, are countersunk from the outside, provide the ability of the molded-over base 12 to fill these countersinks which tend to better hold the assembly together.

Figure 6:
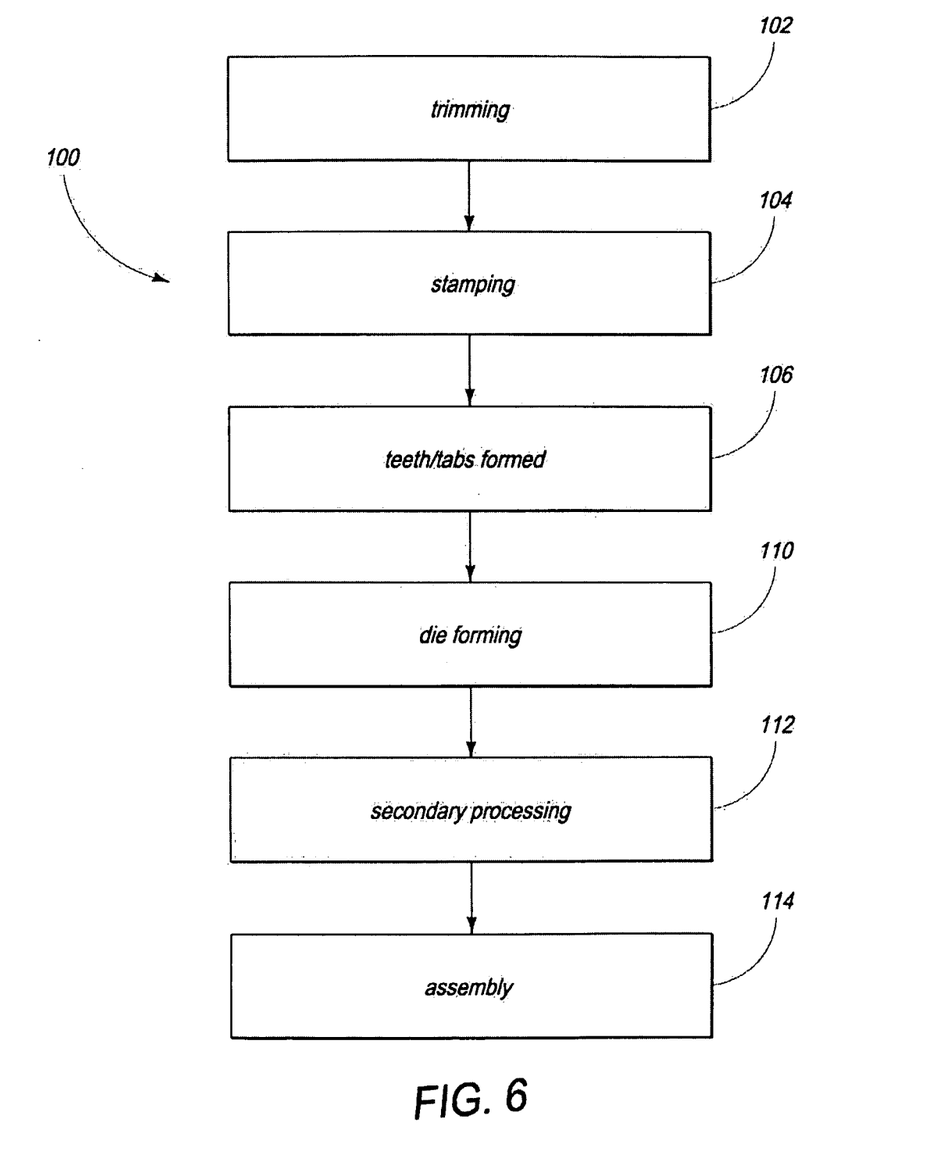
FIG. 6 is a flow chart of the method of manufacturing the reamer assembly of the invention.

Referring now to FIG. 6, in another embodiment, a method 100 of manufacturing the reamer assembly 10 is provided. The method 100 includes the following steps: In a first step 102, flat stock 46 is trimmed and prepared for die cutting. In a second step 104, the flat stock 46 is die cut to form the appendages 64 connected at a center 66 and, optionally, the perforations 20 are formed at cutting sites 22. Such cutting sites 22 may, at this time, optionally be formed into cutting teeth 24 (or during the die forming step 110 or in subsequent processing steps) In a third step 106, teeth 24 are formed in the die cut flat stock 46, thereby greatly reducing the complexity of forming such teeth, as forming on a pre-formed, flat blank 46 is considerably simpler than forming such teeth on a hemisphere, which would be the case after forming of the body 14. While still in the flat state, the tabs 44 are formed as well. In a fourth step 110, the die cut flat stock 46 is formed into a hemispherical shape as shown in FIG. 1. In a fifth step 112, secondary processing is performed, such as sharpening the teeth 24 and deburring the body 14. The body 14 is then ready to be affixed via its tabs 44 to the base 12.

In the embodiment (see FIGS. 4A and 4B), having interlocks 82' and 84', the male interlock 82' is folded into the recess interlock 84', in a separate step which is taken after die-forming the basic overall convex cutting form 14. This is accomplished by folding the male interlock 82' upward during the stamping step 104, or as a subsequent step, and then receiving these interlocks 82' in reliefs (not shown) in the dies (not shown) immediately under the male interlock 82, so that they are not folded into locking engagement with their corresponding recess interlocks 84' until after the final form is die-formed and the adjacent edges 76' are adjacent one another and the interlocks 82' and 84' properly aligned with one another to facilitate the final step of folding the interlocks 82' into the recess interlocks 84'.

Figure 7:
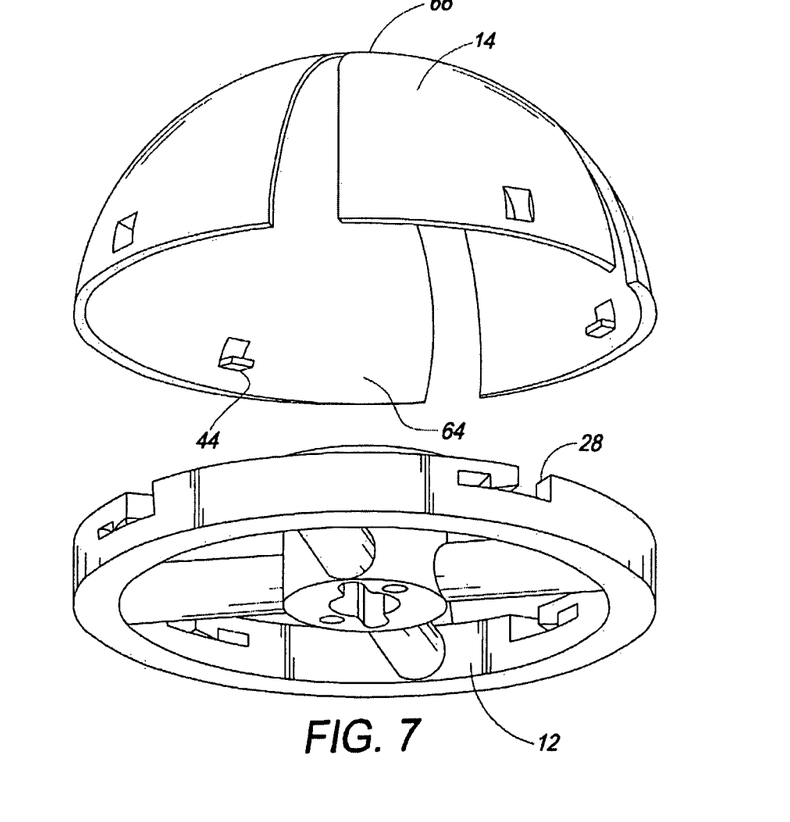
FIG. 7 is a perspective, exploded view showing the preassembled components of the reamer of the invention.

Referring now to FIG. 7, in a final step 114, the cutting body 14 is joined to the base 12, in a mechanical engagement using tabs 44 and bayonet slots 28, or alternatively, as best shown in FIG. 5, by placing the cutting body 14 in a fixture (not shown) and overmolding the base 12 adjacent the equatorial edge 18 of the body.

In an advantage, the invention offers embodiments 46, 50 that permit the disposal of the entire assembly 10 or of the cutting body 14 only.

In an advantage, the appendages 64 assure improved die forming of the body 14 into a final desired shape while at the same time minimizing stress-induced deformation in the body. In other words, the use of appendages 64 assures improved die forming of the body 14 into a final desired shape while at the same time minimizing stress-induced deformation in the body.

In another advantage, the complex teeth 24 can be formed when the body 14 is flat, thereby significantly reducing set up and tool and die costs, while improving accuracy and repeatability.

In another advantage, the complex disks 62 of the invention allow die-forming harder, more durable materials with less warpage than by die-forming a simple disk 56 or partial disk 60.

Multiple variations and modifications are possible in the embodiments of the invention described here. Although certain illustrative embodiments of the invention have been shown and described here, a wide range of modifications, changes, and substitutions is contemplated in the foregoing disclosure. While the above description contains many specifics, these should not be construed as limitations on the scope of the invention, but rather as exemplifications of one or another preferred embodiment thereof. In some instances, some features of the present invention may be employed without a corresponding use of the other features. Accordingly, it is appropriate that the foregoing description be construed broadly and understood as being given by way of illustration and example only, the spirit and scope of the invention being limited only by the appended claims.

What is claimed is:

1. A reamer, which comprises:
   a) a base comprising a wall having an outer base surface providing a perimeter extending from a lower base surface defining an imaginary base plane upwardly to an upper base surface, wherein the base is provided with at least two bayonet slots spaced about the perimeter and extending inwardly into a thickness thereof from the outer base surface, the base having an interface for mating with a holder;
   b) a hemispherical-shaped cutting dome extending from an apex to a lower edge comprising a lower edge inner surface, the dome being rotatable about a longitudinal axis that is perpendicular to a theoretical equatorial plane of the hemisphere and that passes through the apex of the dome, wherein the dome has an outer surface presenting multiple cutting sites comprising apertures suitable for passing debris into a cavity defined by an inner surface of the dome where the debris may accumulate, and wherein there are at, least two tabs formed from the dome and extending inwardly into the cavity of the dome, the tabs beig generally parallel to the theoretical equatorial plane, and
   c) wherein the lower edge inner surface of the dome contacts the outer base surface with one of the dome tabs received in one of the base bayonet slots to thereby connect the dome to the base.

2. The reamer of claim 1, wherein the base is molded of a biocompatible plastic.

3. The reamer of claim 2, wherein the base is characterized as having been insert molded inside the dome.

4. The reamer of claim 2, wherein the base is characterized as having been over-molded into the dome.

5. The reamer of claim 1 wherein each dome tab is lockable in a respestive base bayonet slot when the reamer is rotated in a cutting direction.

6. The reamer of claim 1 wherein each base bayonet slot includes an arm with a spur that helps maintain a respective dome tab locked into the base bayonet slot.

7. The reamer of claim 1 wherein each dome tab is unlockable from a respective base bayonet slot when the reamer is rotated opposite a cutting direction, thereby permitting disassembly of the cutting dome from the base.

8. The reamer of claim 1, wherein the cutting dome is characterized as having been progressive die formed.

9. The reamer of claim 1, wherein the cutting dome is characterized as having been die formed of a stamped, flat metal blank into a form resembling a Maltese cross.

10. The reamer of claim 1, wherein the cutting dome is characterized as having been die-formed of a stamped, flat metal blank having three extending appendages connected at a center.

11. The reamer of claim 1, wherein the cutting dome is characterized as having been die-formed of stamped, flat metal blank having two extending appendages connected at a center.

12. The reamer of claim 1, wherein the cutting dome is characterized as having been die-formed of a stamped, flat metal blank.

13. The reamer of claim 1 wherein each base bayonet slot includes a spur tending to lock a respective dome tab in the bayonet slot.

14. A method of making the cutting dome for the reamer of claim 1, including the steps of:
   a) stamping a blank out of flat metal, the stamping forming appendages on the flat metal connected at a center thereof; and
   b) die-forming the blank into the cutting dome.

15. The method of claim 14 including stamping cutting perforations and, adjacent thereto, raised tooth sites into the blank.

16. The method of claim 14 including progressive die-forming the blank.

17. The method of claim 14 including stamping second locking interfaces into the blank.

18. The method of claim 14 including die-forming second locking interfaces into the blank.

19. The method of claim 14 including stamping male tabs and female recesses on adjacent sides of the appendages of the blank, wherein the tabs and recesses are folded one into the other.

20. The method of claim 19 including folding one of the male tabs so that it enters into a corresponding adjacent interlocking female recess, thereby reinforcing the cutting dome.

21. The reamer of claim 1 wherein the outer base surface includes a ledge upon which the dome is supported.

22. The reamer of claim 21 wherein an outer surface of the ledge is formed by a first plurality of radii radiating from a focal point on the longitudinal axis of the cutting dome and wherein the outer surface of the cutting dome is formed of a second plurality of the radii.

23. A method of making the cutting dome for the reamer of claim 1, including the steps of:
   a) stamping a blank out of flat metal, the stamping forming appendages on the flat metal connected at a center thereof, wherein male tabs and female recesses are thusly formed on adjacent sides of the appendages; and
   b) die-forming the blank into the cutting dome with the tabs and recesses mating with each other.

24. The reamer of claim 1 wherein the interface comprises a retaining bar having a length extending along a second longitudinal axis of the bar to spaced apart terminal ends permanently attached to an inner surface of the base opposite the outer surface thereof.

25. The reamer of claim 24 wherein the interface comprises a central retaining bar structure substantially centered between where the spaced apart terminal ends of the retaining bar attach to the base.

26. A reamer, which comprises:
   a) a hollow dome comprising:
      i) a dome portion of a hemisphere extending from an apex to a lower edge comprising a lower edge inner surface, the dome portion being rotatable about a longitudinal axis that is perpendicular to a first theoretical equatorial plane of the hemisphere and that passes through the apex of the dome portion, wherein the dome portion has an outer surface presenting multiple cutting sites comprising apertures suitable for passing debris into a cavity defined by an inner surface of the dome where the debris may accumulate;
      ii) two opposed first. edge portions of the lower edge residing on the first theoretical equatorial plane, wherein a second theoretical plane perpendicular to the first theoretical equatorial plane intersects the longitudinal axis with the two first edge portions residing on the first theoretical equatorial plane;
      iii) two second edge portions of the lower edge spaced from the first theoretical equatorial plane toward the apex, wherein one second edge portion resides on opposite sides of the second theoretical plane disposed between and connected to the first edge portions; and
      iv) wherein there are at least two tabs formed from the dome and extending inwardly into the cavity of the dome, the tabs being generally parallel, to the first theoretical equatorial plane;
   b) a base comprising a wall having an outer base surface providing a perimeter extending from a lower base surface defining an imaginary base plane upwardly to an upper base surface, wherein the base is provided with at least two bayonet slots spaced about the perimeter and extending inwardly into a thickness thereof from the outer base surface, the base having an interface for mating with a holder, and
   c) wherein the lower edge inner surface of the dome contacts the outer base surface with one of the dome tabs received in one of the base bayonet slots to thereby connect the dome to the base.

27. The reamer of claim 26 wherein the each base bayonet slot includes an arm with a spur that helps maintain a respective dome tab locked into the base bayonet slot.

28. The reamer of claim 26 wherein the outer base surface includes a ledge upon which the dome is supported, an outer surface of the ledge formed by a first plurality of radii radiating from a focal point on the longitudinal axis of the cutting dome and wherein the outer surface of the cutting dome is formed of a second plurality of the radii.

29. A reamer, which comprises:
   a) a base comprising an annular wall having an outer base surface providing an annular perimeter extending from a lower base surface defining an imaginary base plane upwardly to an upper base surface, wherein the base is provided with at least two bayonet slots spaced about the annular perimeter and extending inwardly into a thickness thereof from the outer base surface, the base having an interface for mating with a holder;
   b) a hemispherical-shaped cutting dome extending from an apex to a lower edge comprising a lower edge inner surface, the dome being rotatable about a longitudinal axis that is perpendicular to a theoretical equatorial plane of the hemisphere and that passes through the apex of the dome, wherein the dome has an outer surface presenting multiple cutting sites comprising apertures suitable for passing debris into a cavity defined by an inner surface of the dome where the debris may accumulate, and wherein there are at least two tabs formed from the dome and extending inwardly into the cavity of the dome, the tabs being generally parallel to the theoretical equatorial plane, and
   c) wherein the entire lower edge inner surface of the dome contacts the outer base surface with one of the dome tabs received in one of the base bayonet slots to thereby connect the dome to the base.

* * * * *

UNITED STATES PATENT AND TRADEMARK OFFICE
CERTIFICATE OF CORRECTION

| | | |
|---|---|---|
| PATENT NO. | : 8,679,124 B2 | Page 1 of 1 |
| APPLICATION NO. | : 11/960754 | |
| DATED | : March 25, 2014 | |
| INVENTOR(S) | : Lechot et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1609 days.

Signed and Sealed this
Seventh Day of July, 2015

Michelle K. Lee
*Director of the United States Patent and Trademark Office*

UNITED STATES PATENT AND TRADEMARK OFFICE
CERTIFICATE OF CORRECTION

| | | |
|---|---|---|
| PATENT NO. | : 8,679,124 B2 | Page 1 of 1 |
| APPLICATION NO. | : 11/960754 | |
| DATED | : March 25, 2014 | |
| INVENTOR(S) | : Andre Lechot et al. | |

It is certified that error appears in the above-identified patent and that said Letters Patent is hereby corrected as shown below:

Column 5, line 48, Claim 1, after the word "at" delete the ","

Column 5, line 50, Claim 1, delete "beig" and insert --being--

Column 5, line 63, Claim 5, delete "respestive" and insert --respective--

Column 7, line 31, Claim 26, after the word "parallel" delete the ","

Signed and Sealed this
Eighth Day of December, 2015

Michelle K. Lee
*Director of the United States Patent and Trademark Office*